United States Patent
Basilion

(10) Patent No.: US 9,271,653 B2
(45) Date of Patent: Mar. 1, 2016

(54) INTRA-OPERATIVE MOLECULAR IMAGING

(71) Applicant: Case Western Reserve University, Cleveland, OH (US)

(72) Inventor: James Basilion, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 31 days.

(21) Appl. No.: 14/014,889

(22) Filed: Aug. 30, 2013

(65) Prior Publication Data
US 2014/0088384 A1 Mar. 27, 2014

Related U.S. Application Data

(63) Continuation-in-part of application No. 13/288,611, filed on Nov. 3, 2011, now Pat. No. 9,192,302, which is a continuation of application No. 11/811,818, filed on Jun. 12, 2007, now Pat. No. 8,078,264.

(60) Provisional application No. 61/695,046, filed on Aug. 30, 2012.

(51) Int. Cl.
*A61B 5/00* (2006.01)
*A61B 19/00* (2006.01)
*A61N 5/10* (2006.01)
*A61B 18/20* (2006.01)

(52) U.S. Cl.
CPC ............. *A61B 5/0071* (2013.01); *A61B 5/4836* (2013.01); *A61B 19/2203* (2013.01); *A61B 19/50* (2013.01); *A61N 5/1084* (2013.01); *A61B 5/7264* (2013.01); *A61B 18/20* (2013.01); *A61B 2019/504* (2013.01)

(58) Field of Classification Search
CPC ............... A61B 5/0059; A61B 5/0071; A61B 2019/5231; A61K 49/0017
USPC .................................................. 600/473, 476
See application file for complete search history.

(56) References Cited

U.S. PATENT DOCUMENTS

| | | | | |
|---|---|---|---|---|
| 5,515,864 | A * | 5/1996 | Zuckerman | 600/311 |
| 6,152,870 | A * | 11/2000 | Diener | 600/107 |
| 7,977,058 | B2 * | 7/2011 | Low | 435/7.1 |
| 2004/0087862 | A1 * | 5/2004 | Geng | 600/473 |
| 2012/0116230 | A1 * | 5/2012 | Basilion | 600/473 |

* cited by examiner

*Primary Examiner* — Jonathan Cwern
(74) *Attorney, Agent, or Firm* — Tarolli, Sundheim, Covell & Tummino LLP

(57) ABSTRACT

A system for detecting tumor margins includes a topical protease-specific, fluorescence imaging probe that is activatable by enzymatic activation to produce a visually differentiated signal upon topical application to a targeted cancer cell that secretes an enzyme that activates the protease-specific, fluorescence imaging probe, an applicator for topically administering the imaging probe to the cancer cell; and an imaging device to detect activation of the imaging probe administered to the cancer cell.

20 Claims, 13 Drawing Sheets

Figs. 10A-B

INTRA-OPERATIVE MOLECULAR IMAGING

RELATED APPLICATION

This application is a Continuation-in-Part of U.S. patent application Ser. No. 13/288,611, filed Nov. 3, 2011, which is a Continuation of patent application Ser. No. 11/811,818, filed Jun. 12, 2007 (Now U.S. Pat. No. 8,078,264), and claims priority from U.S. Provisional Application No. 61/695,046, filed Aug. 30, 2012, the subject matter, which is incorporated herein by reference in its entirety.

BACKGROUND

Conventional intra-operative imaging (IOI) may improve surgical results. However, conventional 101 may be limited by lack of resolution (e.g., approximately 0.9 mm) IOI may include, for example, MR (magnetic resonance) guided imaging. Conventional IOI may suffer from cramped surgical fields, surgery induced changes in MR enhancing tissues, difficulty in differentiating scar tissue from diseased tissue in patients that have previously undergone surgery, and so on. Thus, even "complete resections" guided by conventional IOI may not remove all abnormal cells associated with diseased tissue. For example, malignant cells that have infiltrated or are beginning to infiltrate at a tumor brain margin may not be removed.

Intra-operative MRI (magnetic resonance imaging) was introduced in 1997 for brain tumor surgery. Intra-operative MRI has been demonstrated to facilitate decreasing tumor burden over non-IOI augmented microscopic surgery. Intra-operative MRI may include, for example, gross initial excision followed by finer image-guided excision. Intra-operative MRI guided techniques may also include excision followed by image-guided radiological therapy. Conventional surgical excision aided by conventional IOI, limited as it is, has facilitated prolonging survival and quality of life.

Malignant gliomas affect approximately 15,000 people per year in the United States and remain difficult to treat. These gliomas present as focal masses within the brain substance and exhibit infiltrating margins in normal brain. Malignant gliomas produce a steady decline in quality of life and produce cumulative neurological and medical morbidities. Conventional therapeutic treatments (e.g., surgical excision, radiation) for malignant brain tumors (e.g., glioblastoma multiform) are at best palliative. These therapeutic treatments may include intra-operative navigational techniques and electrocorticographic mapping of involved motor and language areas. Other malignancies, brain diseases and abnormalities also remain difficult to treat. For example, treatment of epilepsy involves surgical resection of epileptic foci responsible for generating seizure activity in patients. The same technical challenges, to identify and mark abnormal cells or diseased tissues, posed for surgical resection of malignant gliomas exist for surgical resection of epileptic foci. Various imaging techniques and surgical techniques continue to evolve to meet these challenges.

Outside the brain, intra-operative navigational techniques and electrographic mapping are employed in the treatment of heart arrhythmias. Arrhythmias can occur in a healthy heart and be of minimal consequence. They also may indicate a serious problem and lead to heart disease, stroke or sudden cardiac death. Heat mediated and cryo-ablation are two conventional therapeutic treatments for heart arrhythmias. But like surgical techniques employed in the brain, the treatment can be harmful and affect a larger area of tissue than is therapeutically required. This is largely due to a lack of precision and resolution of current intra-operative imaging techniques applied for these interventions.

In some conventional examples, to attempt to identify abnormal cells, microscopic IOI techniques are combined with intravenously provided fluorescents dyes or drugs that home to diseased tissue and that may provide signals that are useful for imaging. These agents tend to fluoresce in the visible range. Unfortunately, significant background autofluorescence from the patient may make unambiguous detection of labeled diseased tissue problematic. These agents typically require systemic administration at doses that may approach those of therapeutics. Thus, translating these agents from clinical trial may be expensive and labor intensive, if possible at all. These agents also tend not to be associated with disease-specific molecular targets per se and thus do not provide the ability to exploit differential expression of molecular targets for added information during resection. Other techniques employing NIRF probes and systemic administration may require unacceptable intravenous dose requirements, unacceptable time to "develop" signal, and may depend on the vasculature for delivery, which may not provide probes to the region of interest.

SUMMARY

Embodiments described herein relate to a system for determining cancer margins. The system includes a topical protease-specific, fluorescence imaging probe that is activatable by enzymatic activation to produce a visually differentiated signal upon topical application to a targeted cancer cell that secretes an enzyme that activates the protease-specific, fluorescence imaging probe. The system also includes means for topically administering the imaging probe to the cancer cell and an imaging device to detect activation of the imaging probe administered to the cancer cell.

In some embodiments, the enzyme can be one of Cathepsin B, and Cathepsin L. The system can further include an imaging logic to detect a tumor margin, based, at least in part, on the activation of the fluorescent imaging probe. The cancer cell can be at least one of a breast cancer cell, glioma cell, skin cancer cell, prostate cancer cell, or glioma and the imaging logic can detect the breast cancer cell, glioma cell, skin cancer cell, prostate cancer cell, or glioma, based, at least in part, on the activation of the fluorescent imaging probe.

In some embodiments, the system can further include a radiologic plan logic to plan a surgical or radiologic treatment based, at least in part, on a detection of a tumor margin, and a detection of an infiltrating cell.

In other embodiments, the system can include an ablative laser plan logic to plan an ablative laser treatment based, at least in part, on a detection of a tumor margin, and a detection of an infiltrating cancer cell. The ablative laser plan logic can be configured to control, at least in part, an ablative laser.

Other embodiments described herein relate to a method that includes topically applying a protease-specific, fluorescence imaging probe to an area in which a cancer cell may be located. The probe can be activatable by enzymatic activation to produce a visually differentiated signal upon topical application to the cancer cell. The cancer cell can express an enzyme that activates the protease-specific, fluorescence imaging probe. The method further includes detecting, with an imaging device, imaging probe activation induced by an interaction between the imaging probe and the enzyme expressed by the cancer cell.

In some embodiments, the enzyme can be one of Cathepsin B, and Cathepsin L. The system can further include an imaging logic to detect a tumor margin, based, at least in part, on the activation of the fluorescent imaging probe. The cancer cell being at least one of a breast cancer cell, glioma cell, skin cancer cell, prostate cancer cell, or glioma.

Still other embodiments described herein relate to a method for performing a medical procedure. The method includes topically applying a protease-specific, fluorescence imaging probe to an area in which a targeted cancer cell may be located. The imaging probe is activatable by enzymatic activation to produce a visually differentiated signal upon topical application to the cell. The cancer cell expresses an enzyme that activates the protease-specific, fluorescence imaging probe. The method further includes imaging the cell to which the probe is topically applied.

In some embodiments, the enzyme can be one of Cathepsin B, and Cathepsin L. Topical application can include spraying the imaging probe onto a tissue sample containing the cell. The tissue sample can be a biopsy that is obtained from the animal. The cancer cell can be at least one of a breast cancer cell, glioma cell, skin cancer cell, prostate cancer cell, or glioma.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Figure 1:
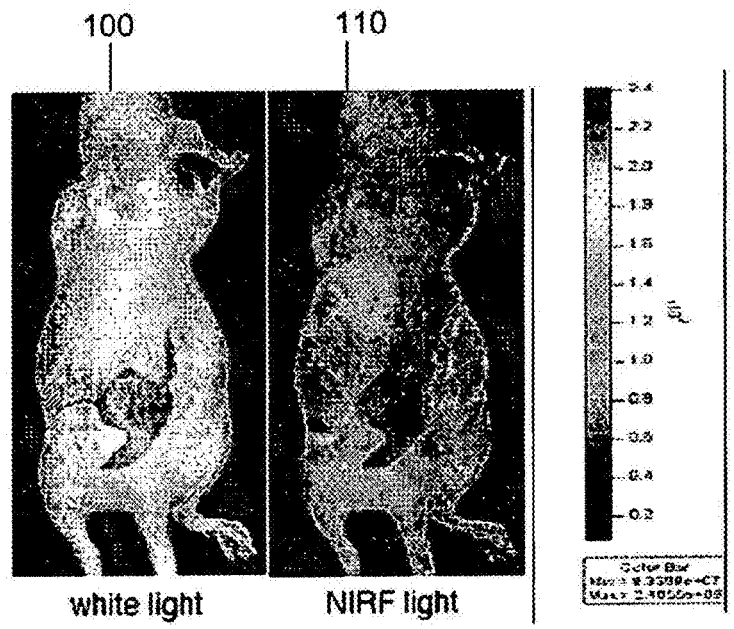
FIG. 1 illustrates an animal imaged before administration of a NIRF probe.

Example systems and methods described herein concern identifying abnormal cells and/or diseased tissue without using intravenously provided imaging agents. To identify and thus to facilitate removing these abnormal cells, microscopic Intra-Operative Imaging (IOI) techniques are combined with topically applied molecular imaging markers for abnormal cells and/or diseased tissue. One with ordinary skill in the art will appreciate that identifying abnormal cells and diseased tissue may include labeling abnormal cells and/or labeling secreted .molecular markers no longer associated with the abnormal cell. The example IOI techniques employ lower dose levels of optical imaging probes than conventional "near-therapeutic levels" techniques. Example techniques may involve topically administering either sub-pharmacologic doses of an agent or doses expected to produce a pharmacologic effect but not a toxic or other biological effect. Thus, the imaging agent is not delivered via intravenous injection, but rather via topical application, which facilitates localized probe diffusion. Specifically, the probe is topically delivered to the targeted tissue in a hydrophobic/hydrophilic solution that facilitates localized probe diffusion. An example hydrophobic/hydrophilic solution may include Dimethyl Sulfoxide (DMSO). The imaging agent may, for example, be detectable in the infrared (IR) spectrum.

In one example, a targeted fluorescent imaging probe can be topically applied as needed during surgery to interactively guide a surgeon and/or surgical instrument to remaining abnormal cells. The probe may be applied locally in low concentration, making it unlikely that pharmacologically relevant concentrations are reached. In one example, excess material may be removed (e.g., washed off) after a period of time (e.g., incubation period). In one example, the probe may target matrix metallproteases (MMPs) that are secreted from brain cells. Another example probe may be directed towards other families of proteases (e.g., cysteine proteases). Yet another example probe may be directed toward non-protease disease markers or abnormal cell markers. Probes may be detectable in a range of wavelengths (e.g., 400-900 nm).

Applications may include the use of a NIRF (near infrared) imaging scanner for IOI. The NIRF imaging scanner may facilitate detecting cells with which the topically applied imaging agent has interacted to produce a visually differentiated field. Another example may include a NIRF imaging scanner that facilitates detection of a cellular product secreted from the abnormal cell with which the topically applied imaging agent has interacted to produce a visually differentiated field. In one example, the NIRF scanner may be handheld. In another example, the NIRF scanner may be miniaturized and embedded in an apparatus (e.g., micro-machines, scalpel, neurosurgical cell removal device). Applications may also include acquiring images (e.g., MR, CT, optical) to guide and/or control subsequent activities including, but not limited to, developing a radiologic therapy plan, guiding a surgeon or surgical device (e.g., ablative laser), and so on.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Abnormal cell", as used herein refers to a cell that exhibits an elevated level of a protease or other molecular marker relative to normal cells in the same region of interest. An abnormal cell may exhibit an altered physiological activity relative to normal cells in the same region of interest. An abnormal cell may be, for example, a brain tumor cell that expresses an elevated level of Cathepsin L mRNA or an elevated level of Cathepsin L protein when compared to a nontumor cell located in the same brain region. An abnormal cell may also be, for example, an epileptic cell that exhibits enhanced expression of Cathepsin L compared to a non-epileptic cell. In different examples, an abnormal cell may reside outside the brain and may exhibit an elevated level of protease or other molecular marker compared to a normal cell.

"Computer component", as used herein, refers to a computer-related entity (e.g., hardware, firmware, software, software in execution, combinations thereof). Computer components may include, for example, a process running on a processor, a processor, an object, an executable, a thread of execution, a program, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an' email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, and so on.

"Diseased tissue", as used herein refers to tissue that has an altered biological process or processes with corresponding alteration of cell function or structure and/or changes in gene expression and protein products relative to normal tissues in the same region of interest. Diseased tissue may include for example, an infiltrating glioma cell located at the margin of a brain tumor. Diseased tissue may also include epileptic tissue that exhibits abnormal electrical activity implicated in altering brain function. Diseased tissue may also include heart tissue that displays inappropriate electrical activity implicated in heart arrhythmias. Diseased tissue may also include, for example, Basal Cell Carcinoma, Squamous Cell Carcinoma of the skin, degenerating retina, Barretts esophagus, esophageal displasia, esophageal cancer, breast cancer, and so on.

"Logic", as used herein, includes but is not limited to hardware, firmware, software "and/or combinations thereof to perform a function(s) or an action(s), and/or to cause a function or action from another logic, method, and/or system. Logic may include a software controlled microprocessor, discrete logic (e.g., application specific integrated circuit (ASIC)), an analog circuit, a digital circuit, a programmed logic device, a memory device containing instructions, and so on. Logic may include a gate(s), a combinations of gates, other circuit components, and so on. Where multiple logical logics are described, it may be possible in some examples to incorporate the multiple logical logics into one physical logic. Similarly, where a single logical logic is described, it may be possible in some examples to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, or other means that can be received, transmitted and/or detected.

"User", as used herein, includes but is not limited to, one or more persons, software, computers or other devices, or combinations of these.

FIG. 1 illustrates an animal imaged before administration of a fluorescent imaging probe. Thus, FIG. 1 presents control images of animals with exposed tumors prior to application of a fluorescent imaging probe. Animal 100 illustrates an animal imaged in white light. Animal 110 illustrates an animal imaged in NIRF light.

Topical application of fluorescent imaging probes facilitates identifying abnormal cell markers and facilitates the removal of abnormal cells during surgery. For example, topical application of fluorescent imaging probes (e.g., protease specific fluorescent imaging probes) will image tumor associated markers (e.g., proteases) and delineate tumor margins accurately during resection. These images may facilitate, for example, guiding a surgeon and/or a surgical device (e.g., ablative laser) to non-excised diseased tissue. In another example, topical application of a fluorescent imaging probe will image epileptic associated markers (e.g., proteases). The differentiation of epileptic tissue from non-epileptic tissue may allow for more precise resection of abnormal and/or diseased tissue during surgery. In another example, topical application of a fluorescent imaging probe will image markers associated with cells displaying inappropriate electrical activity in the heart. Imaging of cells displaying inappropriate electrical activity may allow for more precise mapping of a cardiac foci and subsequent removal of this foci. Results of one such topical application are presented in FIG. 2.

Figure 2:
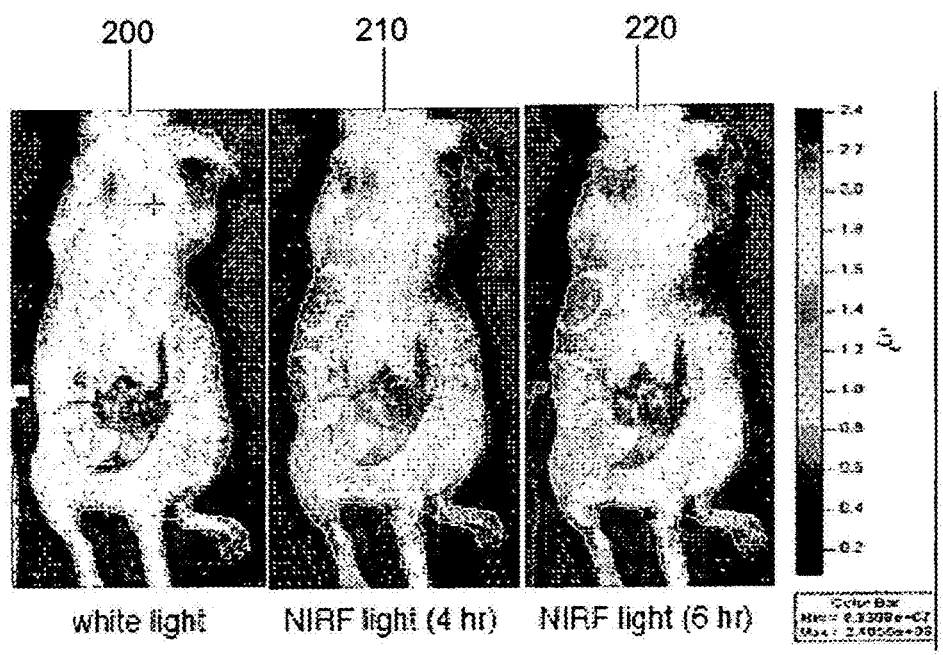
FIG. 2 illustrates an animal imaged after topical application of an activateable NIRF probe that is specific for MMP 2, 7, and 9.

FIG. 2 illustrates in vivo imaging of an animal after topical application of a NIRF probe. The tumor implanted in the animal illustrated in FIG. 2 overexpresses MMPs. While MMPs are described, it is to be appreciated that other proteases (e.g., cysteine proteases, serine proteases) may also be detected. While two proteases are described, it is to be appreciated that proteases from other families may be employed Animal 200 is illustrated in a white light image. After four hours initial probe activation is visible as illustrated by animal 210. By six hours activation of the probe covers substantially all the tumor surface as illustrated by animal 220. While four and six hours are described, it is to be appreciated that NIRF probes having different reaction times (e.g., 5 minutes) may be employed.

Cancer associated proteases hydrolyze peptide bonds in proteins and are involved in various physiological processes, such as digestion, cell cycle regulation, proteolysis, extracellular matrix remodeling, apoptosis and pro-protein activation. Cancer associated proteases are among some of the most consistently overexpressed tumor-associated markers. Cysteine family of proteases (e.g., Cathepsin L, Cathepsin B) have significant increased activity in skin cancers, such as basal cell carcinomas (BCC), squamous cell carcinomas (SCC), and malignant melanomas (MM), breast cancer, prostate cancer and glioblastomas. These proteases have been demonstrated to be sufficient for in vivo imaging using NIRF probes administered intravenously. Thus, some example systems and methods may include topical application of protease-specific fluorescent imaging probes to facilitate delineating tumor margins during resection. In one example, the protease-specific fluorescent imaging probes may be low dose, rapid activating probes that facilitate differentiating normal brain tissue and tumor tissue during surgery. In one example, the NIRF imaging probe may be a Cathepsin specific, optically silent NIRF probe that is activated by Cathepsin B or L. In one example, the NIRF scanner may be an IVIS 200 (Xenogen Inc.) scanner. While Cathepsin specific probes and an IVIS 200 are described, it is to be appreciated that other protease-specific probes and other scanners may be employed. For example, a scanner or NIRF detecting apparatus may be miniaturized and associated with apparatus including a scalpel, a micro-machine, and so on. One example may concern non-cysteine proteases that are over expressed by gliomas and/or other cancers. These non-cysteine proteases mayor may not be secreted by the cells. In one example, probes may depend on enzymatic activation to emit a signal. In another example, probes may irreversibly bind to proteases and visually "tag" expressing cells, thereby identifying them as diseased tissue. In yet another example probes may not require activation, but may accumulate at the target due to enzymatic activity. While fluorescent imaging probes are described, it is to be appreciated that probes detectable in the range of 300 nm to 1 mm may be employed.

Example methods may be better appreciated with reference to flow diagrams. While for purposes of simplicity of explanation, the illustrated methods are shown and described as a series of blocks, it is to be appreciated that the methods are not limited by the order of the blocks, as in different embodiments some blocks may occur in different orders and/or concurrently with other blocks from that shown and described. Moreover, less than all the illustrated blocks may be required to implement an example method. While the figures illustrate various actions occurring in serial, it is to be appreciated that in some examples various actions could occur concurrently, substantially in parallel, and/or at substantially different points in time.

Figure 3:
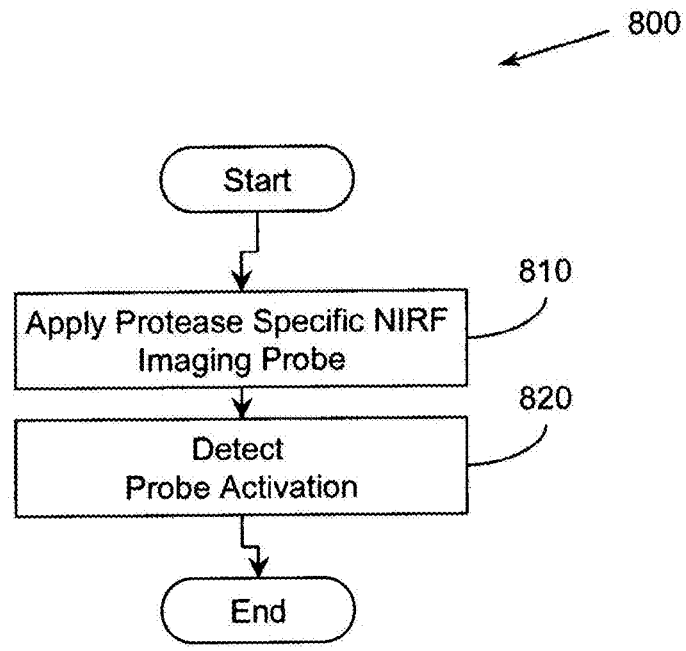
FIG. 3 illustrates an example method associated with identifying abnormal cells.

FIG. 3 illustrates a method 800 associated with identifying abnormal cells. In one example, the abnormal cells may be malignant cells that have infiltrated and/or are beginning to infiltrate at a tumor brain margin. While the brain tumor margin is described, it is to be appreciated that method 800 may be employed more generally to identify abnormal cells that are associated with disease progression. For example, method 800 may be used to visualize foci generating inappropriate electrical activity in the heart and brain thus to facilitate more precise removal of these foci. Method 800 may also be used to visualize abnormal cells and or diseased tissue. Method 800 may be performed in real time during brain or other surgery. Method 800 may include, at 810, topical application of an abnormal cell-marker (e.g., protease specific) optical (e.g., fluorescent) imaging probe and, at 820, detecting probe activation using an imaging device (e.g., handheld NIRF scanner). In one example, image data may be gathered. In one example, this image data may be used to determine, at least in part, a radiological treatment. In another example, this image data may be used to control, at least in part, an automated surgical device (e.g., laser, scalpel, micro-machine) or to aid in manual guidance of surgery. In one example, the image data can be used to control an intra cardiac ablation procedure. In yet another example, the image data may be used to plan and/or control the delivery of a targeted therapeutic. The targeted therapeutic may be delivered, for example, by a micro-electronic machine or micro-machine. It is to be appreciated that method 800 may employ various protease specific NIRF imaging probes and various 101 devices.

Figure 4:
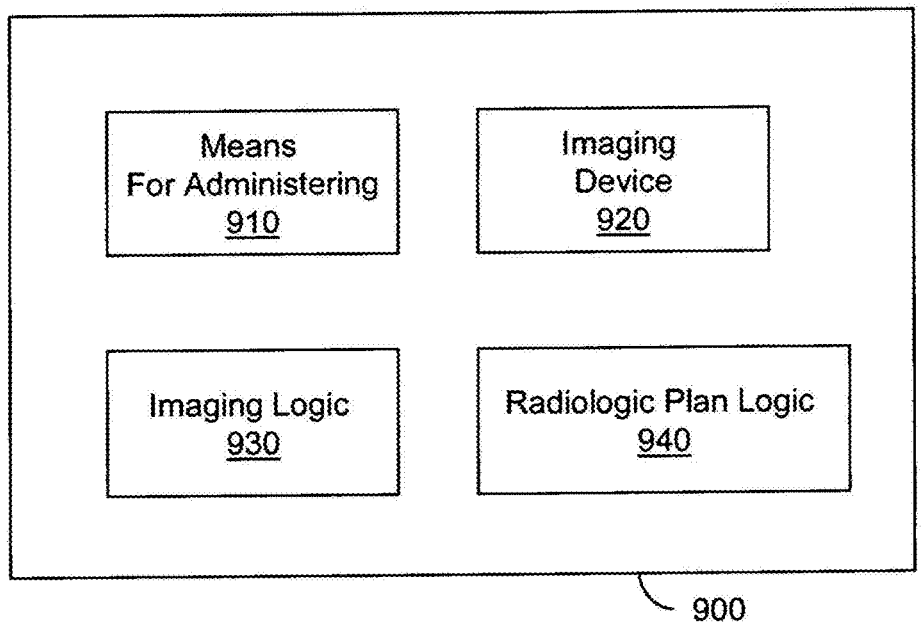
FIG. 4 illustrates an example system associated with identifying abnormal cells.

FIG. 4 illustrates a system 900 associated with identifying abnormal cells. Abnormal cells may include, for example, malignant cells that have infiltrated and/or are beginning to infiltrate at a normal tissue (e.g. brain) tumor margin. Another example of abnormal cells may include cells that display inappropriate electrical activity in the heart and brain. System 900 may include, for example, means 910 for topically administering a probe (e.g., protease specific fluorescent imaging probe) to a diseased tissue (e.g., malignant glioma, metastatic brain malignancy, primary tumor of different origin, epileptic tissue, heart tissue displaying inappropriate electrical activity, Barrets Esophagus tissue, displastic tissue). System 900 may also include, for example, an imaging device 920 to detect an interaction (e.g., activation) of the imaging probe with the diseased tissue. The imaging device 920 may be, for example, a handheld NIRF scanner, a scalpel mounted NIRF apparatus, a micro-machine mounted NIRF apparatus, a camera, and so on. In one example, system 900 may also include an imaging logic 930 to detect a tumor margin, to detect a glioma cell infiltrating a tumor brain boundary, and so on. In another example, system 900 may include an imaging logic 930 to detect cells that display inappropriate electrical activity in the heart and brain, and so on. In one example, system 900 may also include a radiologic plan logic 940 that facilitates planning a radiologic treatment based, at least in part, on the detection of a tumor margin and/or on the detection of an infiltrating cell. It is to be appreciated that system 900 may employ various protease-specific NIRF imaging probes and various 101 devices. In one example, imaging device 920 may be a camera that is connected to an ablative laser scalpel. An image acquired by imaging device 920 may be used to control the ablative laser scalpel to destroy remaining diseased tissue.

Figure 5:
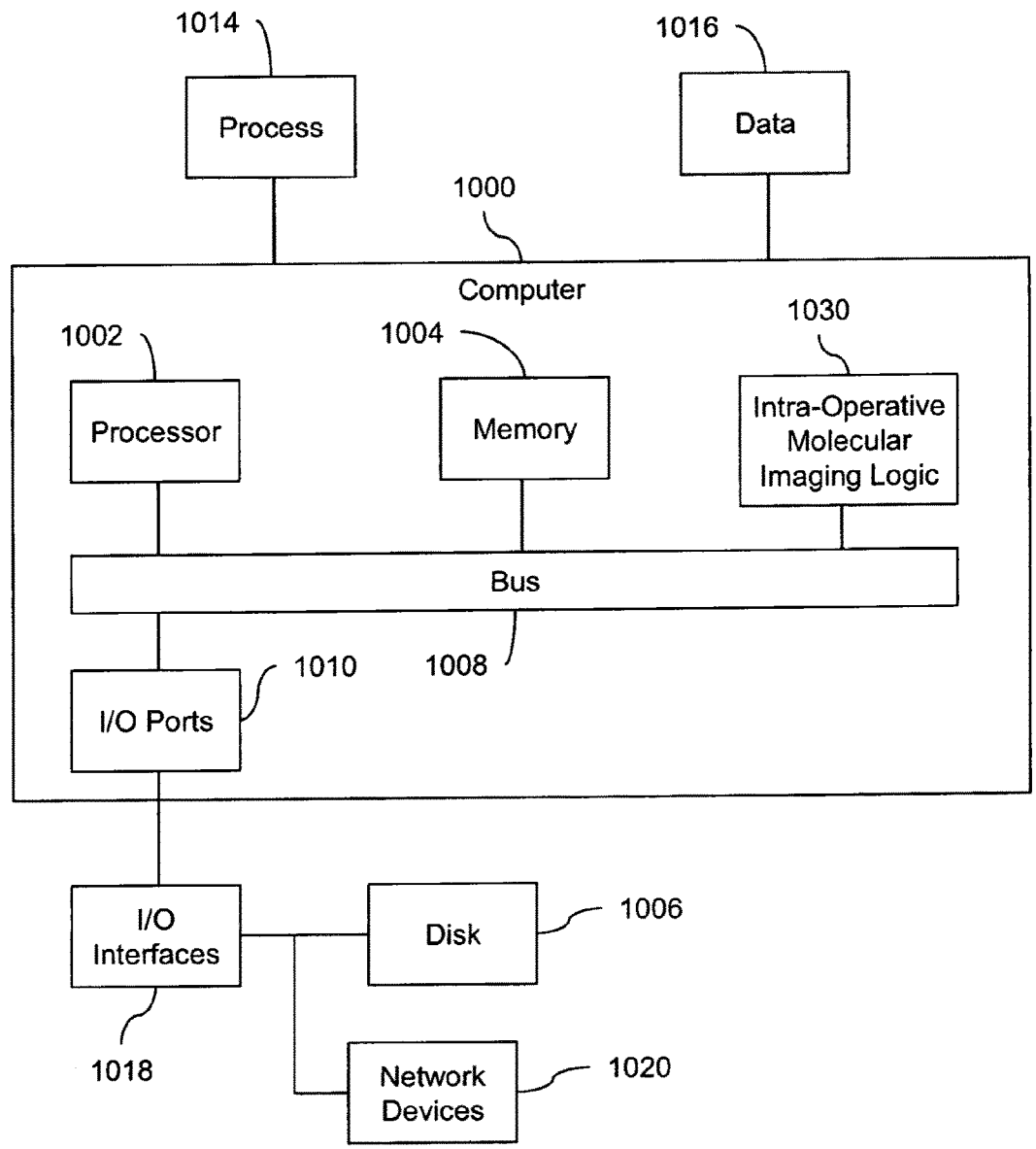
FIG. 5 illustrates an example computing environment in which example systems and methods illustrated herein may operate.

FIG. 5 illustrates an example computing device with which example systems and methods described herein, and equivalents, may operate. The example computing device may be a computer 1000 that includes a processor 1002, a memory 1004, and input/output ports 1010 operably connected by a bus 1008. In one example, the computer 1000 may include an intra-operative molecular imaging logic 1030 to facilitate detecting abnormal cells. In different examples, the logic 1030 may be implemented in hardware, software, firmware, and/or combinations thereof. Thus, the logic 1030 may provide means (e.g., hardware, software, firmware) for receiving image data and means for performing actions including,' but not limited to, determining a radiologic therapy, controlling a surgical device, and so on. While the logic 1030 is illustrated as a hardware component attached to the bus 1008, it is to be appreciated that in one example, the logic 1030 could be implemented in the processor 1002.

Generally describing an example configuration of the computer 1000, the processor 1002 may be a variety of various processors including dual microprocessor and other multi-processor architectures. A memory 1004 may include volatile memory and/or non-volatile memory.

A disk 1006 may be operably connected to the computer 1000 via, for example, an input/output interface (e.g., card, device) 1018 and an input/output port 1010. The disk 1006 may be, for example, a magnetic disk drive, a solid state disk drive, a floppy disk drive, a tape drive, a Zip drive, a flash memory card, and/or a memory stick. Furthermore, the disk 1006 may be a CD-ROM, a CD recordable drive (CD-R drive), a CD rewriteable drive (CD-RW drive), and/or a digital video ROM drive (DVD ROM). The memory 1004 can store a process 1014 and/or a data 1016, for example. The disk 1006 and/or the memory 1004 can store an operating system that controls and allocates resources of the computer 1000.

The bus 1008 may be a single internal bus interconnect architecture and/or other bus or mesh architectures. While a single bus is illustrated, it is to be appreciated that the computer 1000 may communicate with various devices, logics, and peripherals using other busses (e.g., PCIE, SATA, Infiniband, 1394, USB, Ethernet). The bus 1008 can be types including, for example, a memory bus, a memory controller, a peripheral bus, an external bus, a crossbar switch, and/or a local bus.

The computer 1000 may interact with input/output devices via the i/o interfaces 1018 and the input/output ports 1010. Input/output devices may be, for example, a keyboard, a microphone, a pointing and selection device, cameras, video cards, displays, the disk 1006, the network devices 1020, and so on. The input/output ports 1010 may include, for example, serial ports, parallel ports, and USB ports.

The computer 1000 can operate in a network environment and thus may be connected to the network devices 1020 via the i/o interfaces 1018, and/or the i/o ports 1010. Through the network devices 1020, the computer 1000 may interact with a network. Through the network, the computer 1000 may be logically connected to remote computers. Networks with which the computer 1000 may interact include, but are not limited to, a local area network (LAN), a wide area network (WAN), and other networks.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

Example 1

Figure 6A:
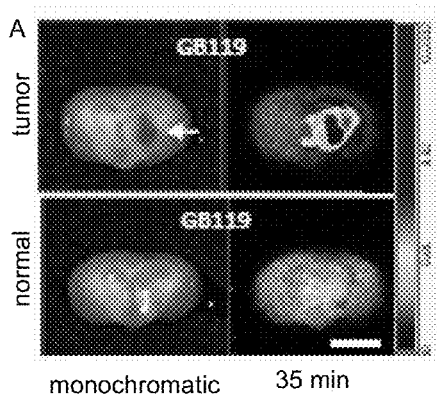
FIGS. 6(A-B) illustrate (A) an image and (B) a graph showing ex vivo application of GB119 to orthotopic brain tumors rapidly activates the probe whereas normal brain tissues do not.
Figure 6B:
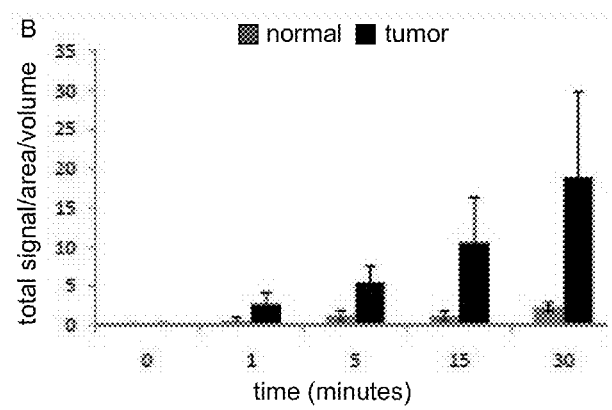

In this Example, we demonstrate the utility and feasibility of topical application of GB119 to assess the presence of cancer in normal tissues. We tested the ability of the probe to be activated when applied ex vivo to tumor tissues, FIG. 6. For these studies mice were unilaterally stereotactically implanted with Gli36DEGER cells to form orthotopic brain tumors. When tumors reached a reasonable size (approximately 10 days of growth) the animals were sacrificed, the brain was removed and cut into 2 mm-thick sections. The sections containing tumor were identified by gross observation and GB119 was topically applied to both the tumor-containing and contralateral sides of the brain that did not contain tumor. The tumor rapidly activated the probe, while the surrounding normal brain and contralateral normal brain did not, FIG. 6. Interestingly, and in agreement with literature describing the location of brain tumor associated proteases, probe activation was greatest at the tumor margins. In inhibitor studies we demonstrated that selectivity of the probe was maintained in the ex vivo setting and our other studies also indicated that topical application of GB119 is able to detect single to small cell clusters that have migrated from the tumor mass.

Figure 7:
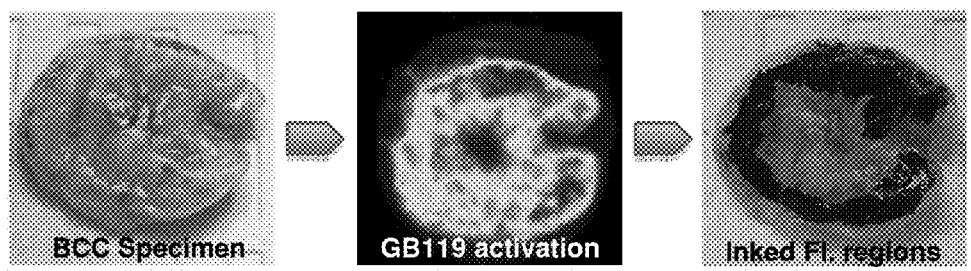
FIG. 7 illustrates images showing ex vivo topical application, imaging and inking of SCC specimen obtained from skin cancer patients.
Figure 8:
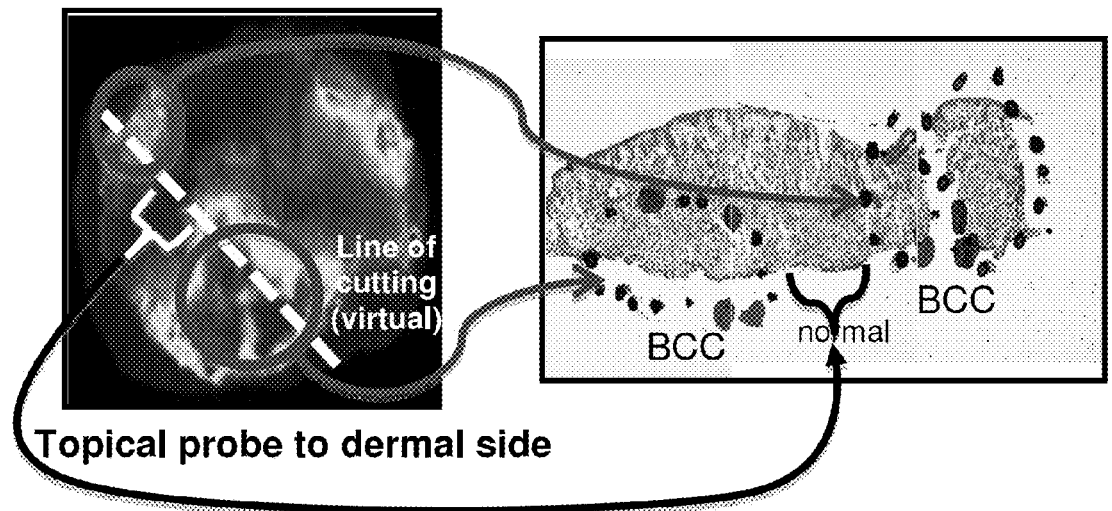
FIG. 8 illustrates images showing ex vivo application of GB119 to the dermal side of skin obtained from skin cancer patients.

To assess the utility of this technology to inform skin cancer removal we have topically applied this probe to either the epidermal or dermal side of skin samples (n=7) removed from patients undergoing Mohs procedure for pathologically confirmed BCC and SCC. For these studies discarded human skin tissue from de-bulking procedures, which occur prior to Mohs resection, were used to determine if topical application of GB119 to skin cancer would result in rapid and robust activation of GB119 (UH IRB Number: 12-05-17, expiration 8/1/13). To ensure global and uniform coverage GB119 was applied to the entire surface of the surgical specimen using an applicator pad impregnated with the imaging probe. Probe activation was regional and occurred minutes after topical application of the probe, FIGS. 7 and 8. Because probe fluorescence is destroyed during fixation and staining, fluorescent regions were inked to identify them during pathological examination, FIG. 7. To demonstrate correlation of the fluorescent regions with cancer cells, frozen sections were then taken through regions of skin containing both activated and unactivated probe and assessed, FIG. 8 (dashed white line, left panel). Sections were fixed, H&E stained, and subjected to pathological analysis by a trained physician for the presence of cancer and its proximity to previously inked areas of tissue. Only cancerous tissue (pathologist hand drawn dotted circles, right panel of FIG. 8) was associated with inked regions, i.e., activated fluorescent probe. No tissue with normal skin pathology was inked indicating that it did not activate the probe. Time course studies, not shown, indicated that probe activation began to reach a maximum within 3-6 minutes.

Figure 9:
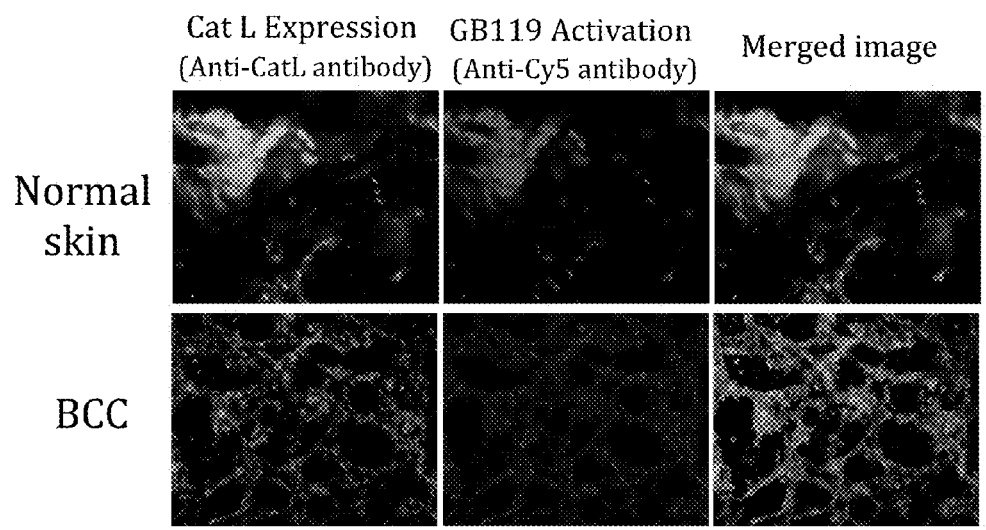
FIG. 9 illustrates images showing immunohistochemistry demonstrating that GB119 is only activated in basal cell carcinomas (BCC) not normal skin.

To further assess the correlation between cancer and activated probe, pathologically confirmed normal skin or BCC tissues were subjected to immunohistochemistry to identify expression of Cathepsin L and activation of GB119 probe. For these studies sections were derived from BCC or normal skin tissue from the same patient that had been treated with topically applied GB119 probe. Tissues were stained with anti-cathepsin L antibody, which reveals the expression of both inactive and active Cathepsin L. (Cathepsins are expressed as zymogens, which require activation. Also, tissue inhibitors of the proteases are present to regulate Cathepsin activity. Studies have demonstrated that Cat L activity is upregulated in skin cancer). Following cathepsin staining the same section was used to identify activated GB119. Since fluorescence of activated GB119 does not survive fixation and immunohistochemistry we utilized a commercially available anti-Cy5 antibody to identify GB119 activation in tissue samples. Cy5 is the fluorophore contained within the probe and is only available as an antigen for the antibody when the quenching moiety of GB119 has be removed by cathepsin activity, data not shown. As FIG. 9 reveals, both normal skin and BCC expressed Cathepsin L (green cells). In contrast, only BCC tissue immunostained for activated GB119 probe (red in bottom center panel, FIG. 9). The merged imaged (right panels, FIG. 9) clearly shows that probe activation is only associated with BCC cells and not normal tissues. These data indicate that normal skin expresses cathepsin L proteases, but not in a biologically active form. In BCC the Cat L has enzymatic activity and is able to activate GB119 probe. These results demonstrate that the GB119 is very selective for activated Cat L proteases. We also saw similar expression patterns of Cat B in normal skin and BCC but with probe activation in BCC only. However, there was much less activation of GB119 by Cat B in BCC tissues (data not shown). This is consistent with our prior studies characterizing GB119 selectivity and the results of our collaborator which both show GB119 is most selective for Cat L proteases.

Figure 10:
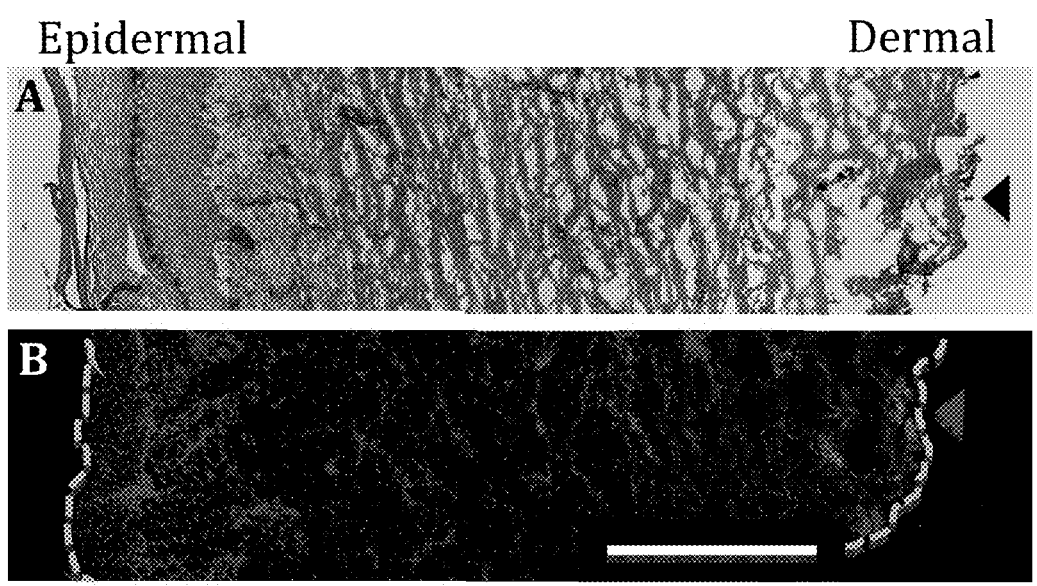
FIGS. 10(A-B) illustrate images showing the depth of penetration of GB119 into skin containing BCC after topical application.

We have also conducted studies to estimate the penetration of the GB119 probe through skin tissue. GB119 was topically applied to tissues containing BCC for 15 minutes and after imaging and inking the specimens were frozen and sagittally cut, FIG. 10. Sections were then immunostained for activated probe and the depth of probe activation was visualized using fluorescence microscopy. GB119 activation formed a gradient from the dermal site of application towards the epidermal side. After approximately 0.5 mm activated GB119 was not detectable (FIG. 10, Panel B) even though cancer cells were present throughout the entire specimen, FIG. 10, Panel A. This suggests that GB119 can migrate approximately 0.5 mm through skin in 15 minutes.

Example 2

Solution to the Unmet Need

Figure 11:
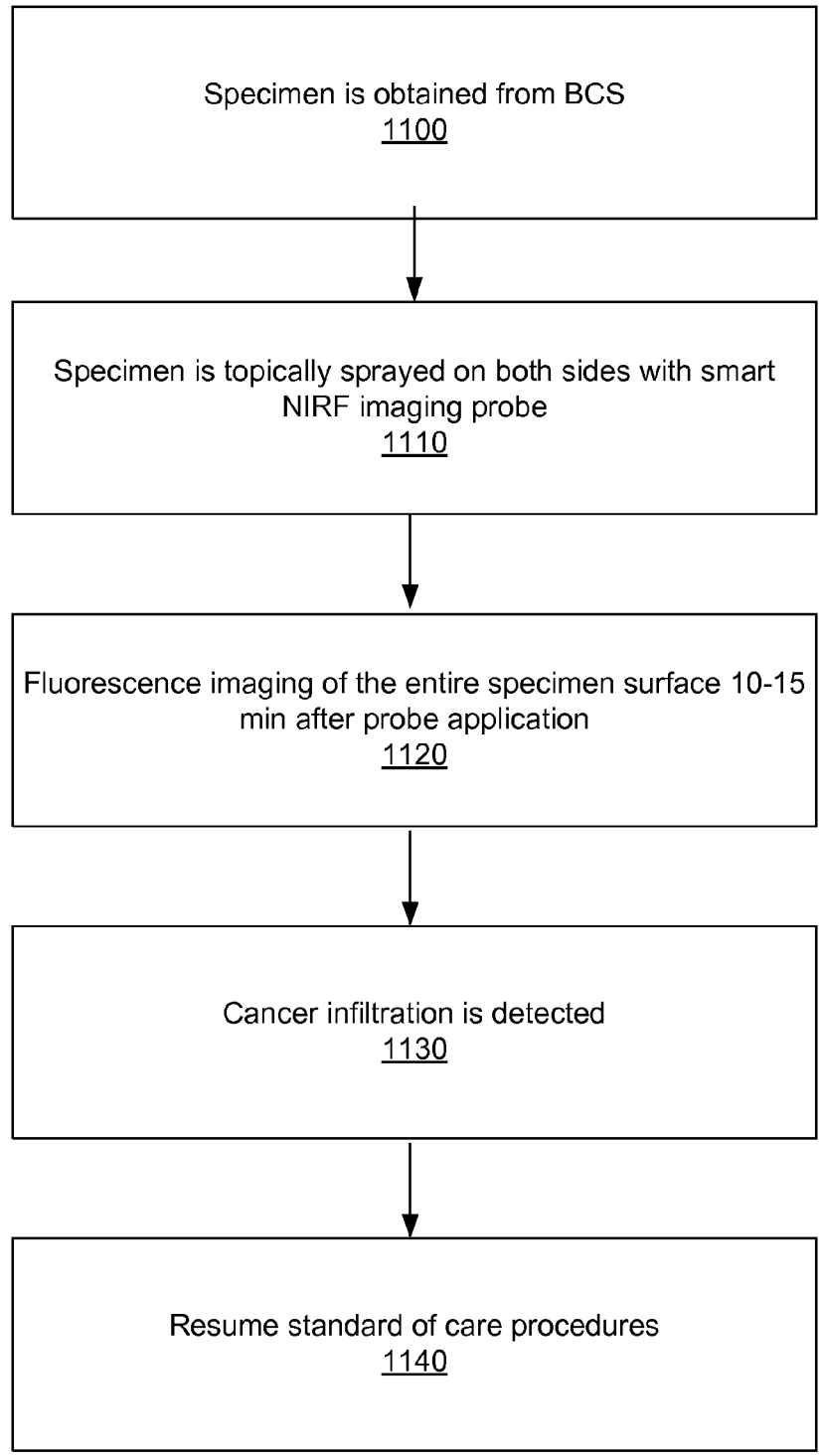
FIG. 11 illustrates an example of a method of assessing lumpectomy margins.

This Example described the use of molecular imaging technologies to provide standardized method to reduce re-excisions and false negatives for breast conservation surgery (BCS) patients. Over expression of tumor-associated proteases in breast cancer cells was used to identify cancer in lumpectomy margins. A quenched or "smart" near infrared fluorescent (NIRF) imaging probe called GB119 that targets cathepsins B and L, which are overexpressed in most breast cancers, can be applied topically to excised lumpectomy specimens. Probe that encounters cathepsin B and/or L proteases will de-quench and fluoresce, i.e., probe activation. Treated tissues will be globally surveyed for probe activation using a commercially available fluorescent multispectral imaging system. Since penetration of the optically silent probe into tissue is limited to approximately 2 mm any fluorescence with spectral characteristics of the activated probe would indicate cancer infiltration into the lumpectomy margin. FIG. 11 shows our approach for assessment of lumpectomy margins.

Figure 12:
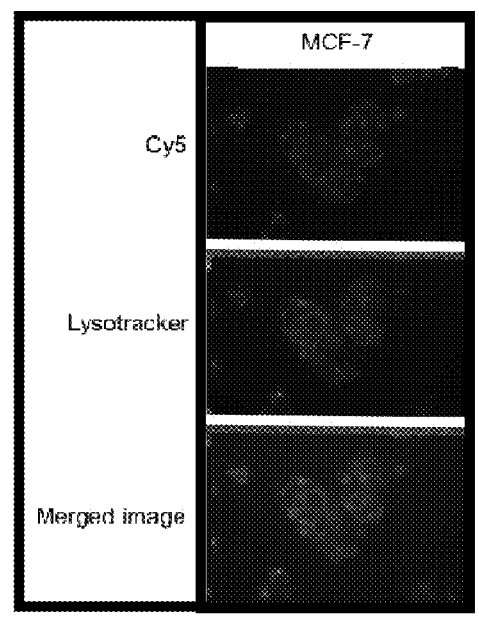
FIG. 12 illustrates images showing MCF-7 cells robustly activate GB119. MCF-7 cells were incubated with GB119 is culutre for 1 hour, fixed and then processed for imaging. Activation of GB119 is visible in the top frame (Cy5) and co localizes with lysosomal markers. Lysosomes is where Cat B and L reside.
Figure 13:
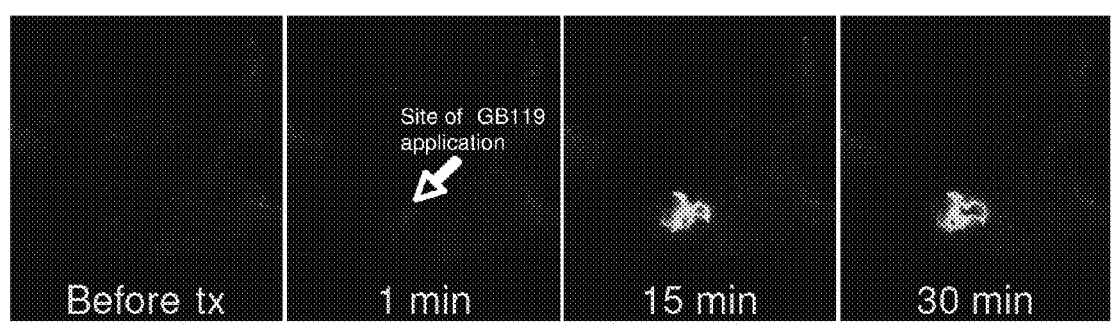
FIG. 13 illustrates images showing activation of GB119 by MCF-7 tumor xenografts.
Figure 14:
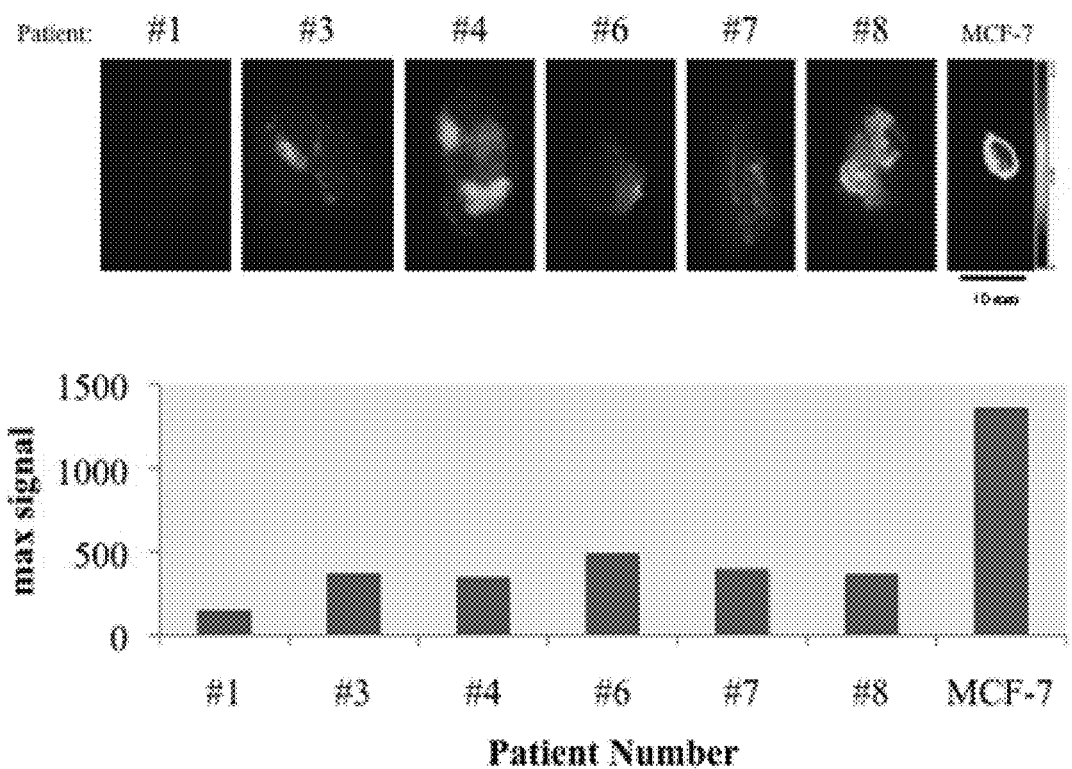
FIG. 14 illustrates images showing GB119 is not activated by normal breast tissues.
Figure 19:
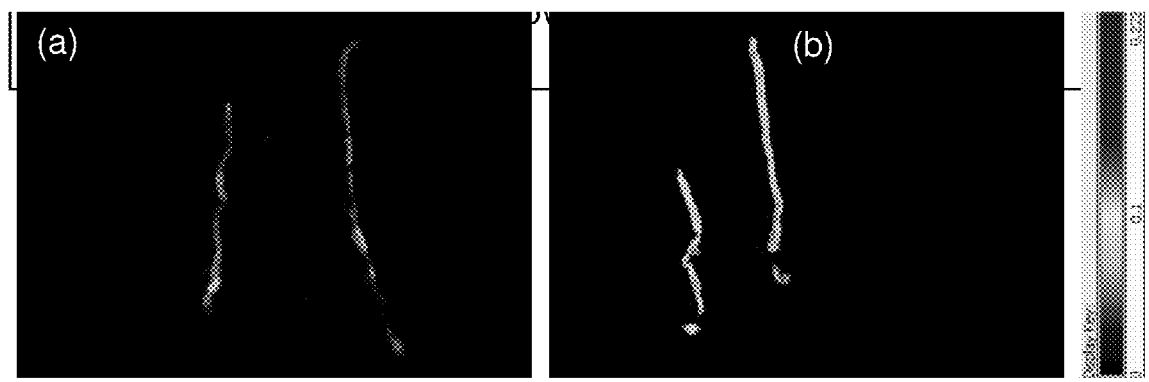
FIGS. 19(A-B) illustrate images showing activation of GB119 imaging probe in ex vivo PCa biopsies specimens Immediately after biopsy, GB119 was topically applied to biopsy specimens. Following a 10 minute incubation specimens were imaged using a Maestro imaging device. (A) Histologically confirmed PCa negative sample showing no activate the probe activation, (B) histologically confirmed PCa positive samples showing probe activation.

We performed several feasibility studies to determine if the proposed approach is sound. We first showed cell lines representative of targeted tissue selectively activate GB119 (Cy5-labeled), FIG. 12 cells not expressing cathepsins B and L do not activate the probe (data not shown). We next showed GB119 could be topically applied to human breast tumors grown in the flanks of mice. MCF-7 cells were used to generate flank tumors in nude mice and the tumors surgically exposed. GB119 dissolved in 100% DMSO was topically applied to the tumor and the animals were imaged over time. As FIG. 13 shows, MCF7 cells rapidly activated the probe with some activation by 1 minute and robust activation within 15 minutes. We have confirmed these findings for other human breast cancer cell lines, e.g. MDA-MB-231 and MDA-MB-468. Normal breast does not activate GB119, FIG. 19.

Figure 15:
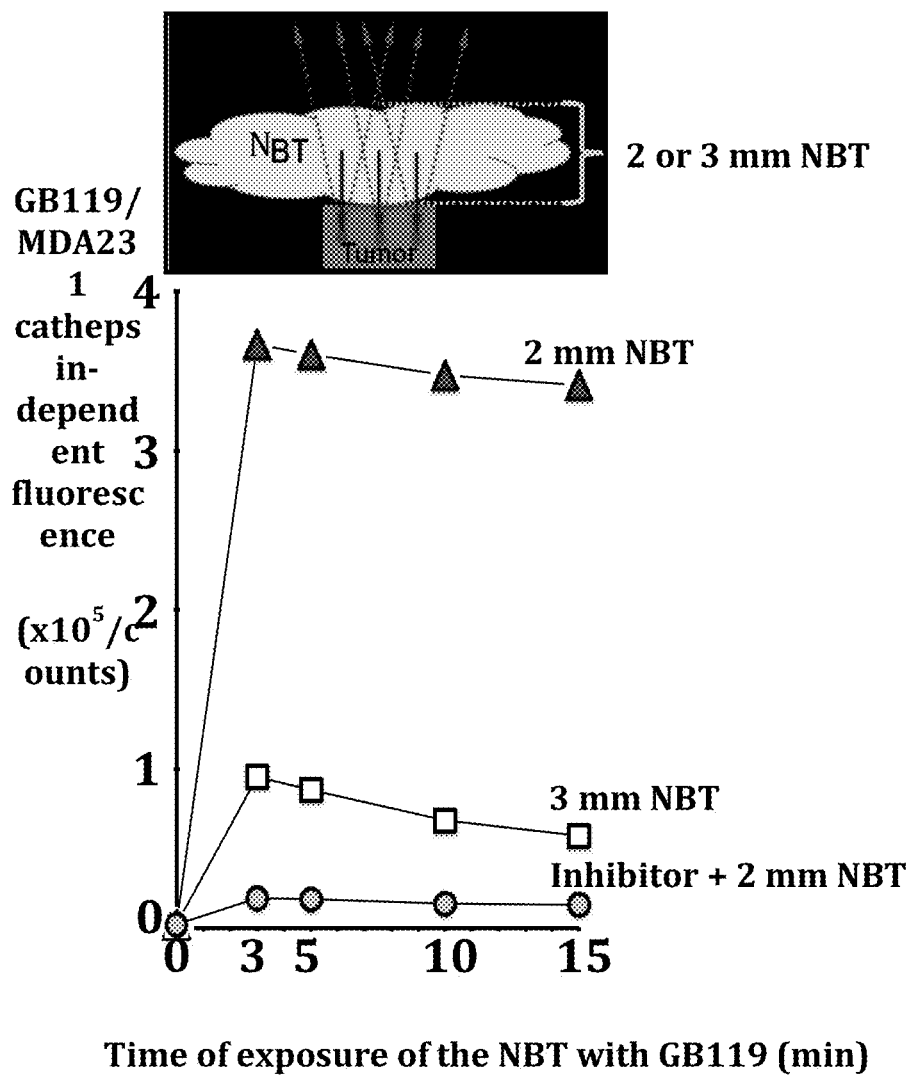
FIG. 15 illustrates a plot showing penetration of probe through Normal Breast Tissue (NBT). Paper disks impregnated with 10 uM GB119 in 100% DMSO were placed on top of each of the different sandwiches and the extent of probe activation was measured over time, triangle=2 mm; sq.=3 mm NBT. As a control for selectivity, a cathepsin inhibitor K11777 was included with GB119, circles. Data was normalized to a sandwich that did not contain any tumor xenograft. NBT=normal breast tissue.
Figure 16:
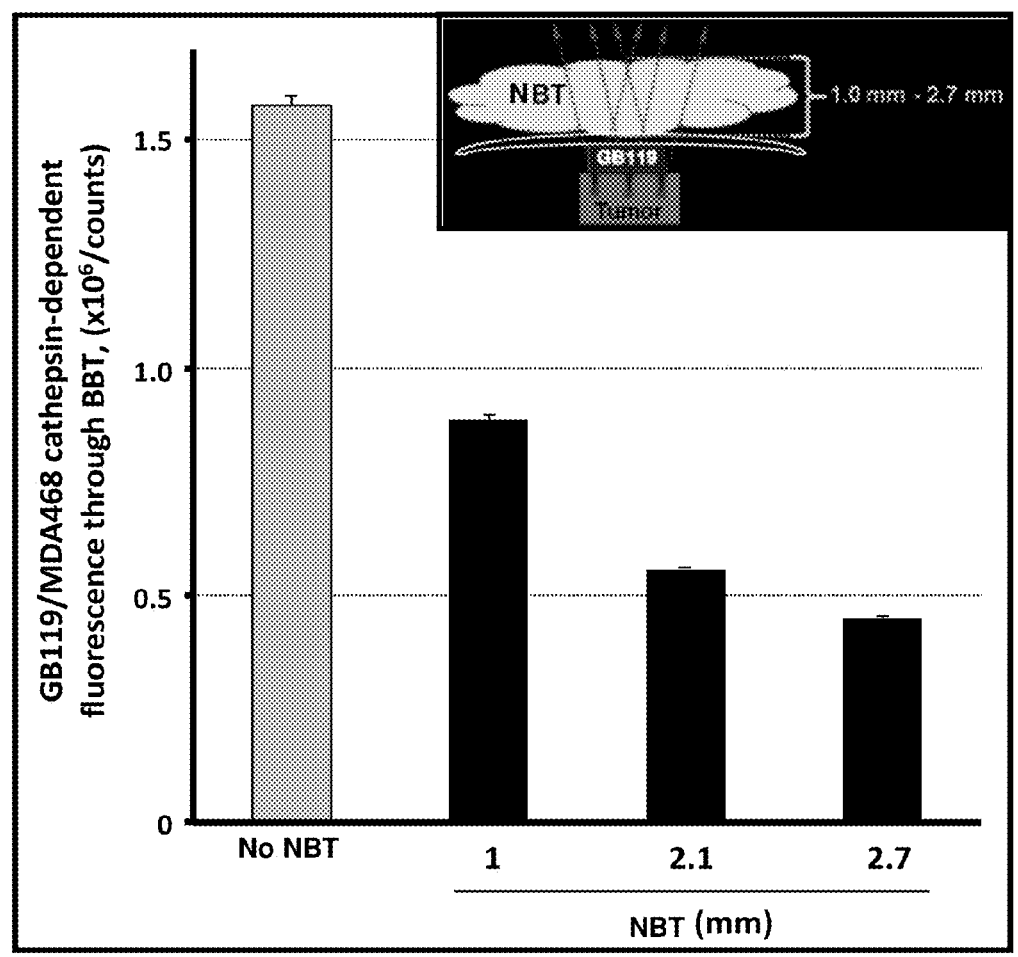
FIG. 16 illustrates a graph showing propagation of light through Normal Breast Tissue (NBT). Xenograft tumors explanted from mice were incubated with probe to generate signal and then covered with a transparent film. Different thicknesses of normal breast tissue (NBT) were placed on top of the tumor and the propagation of fluorescence from activated GB119 through the NBT was measured using a Maestro Imaging Device (Perkin Elmer).

It was found that the GB119 probe, which is hydrophobic, can easily penetrate tissue allowing us to identify the existence of cancer cells within the margins of the lumpectomies as well as on the surface. This feature is unique making it superior to other approaches for assessing lumpectomy margins. We therefore performed a series of studies to determine the limits of probe penetration and detection of cancers. For these studies fresh normal breast tissue (NBT) specimens of differing thickness (obtained from reduction mammoplasty) were placed on top of xenografts derived from MDA-MB-231 cells forming the "sandwich" shown in FIG. 15. Paper applicator disks impregnated with GB119 in 100% DMSO were placed on top of the sandwich and probe penetration was monitored by measuring GB119 fluorescence over time. These data demonstrate that the penetration of the probe through normal breast tissue and its activation by breast cancer occurs very rapidly, within 3 minutes. Further these results suggest that the probe is effective at detecting cancer through 2 mm of tissue, but not through 3 mm of tissue. Since the detection of probe activation not only depends on the diffusion of probe into the tissue but also on propagation of light from activated probe out of the tissue, we also measured the effect of different thicknesses of normal breast tissue on detection of activated probe. For this study GB119 was applied directly to tumor tissue and then covered with transparent film to generate a consistent source of fluorescence. Different thicknesses of normal breast tissues were sequentially placed on the covered fluorescent tumor and the penetration of light was measured, FIG. 16. These data show that light is attenuated by thicker NBT and demonstrate that tumor detection by this technology in lumpectomy tissues is limited to approximately 2 mm, optimal for assessing clear margins.

Figure 17:
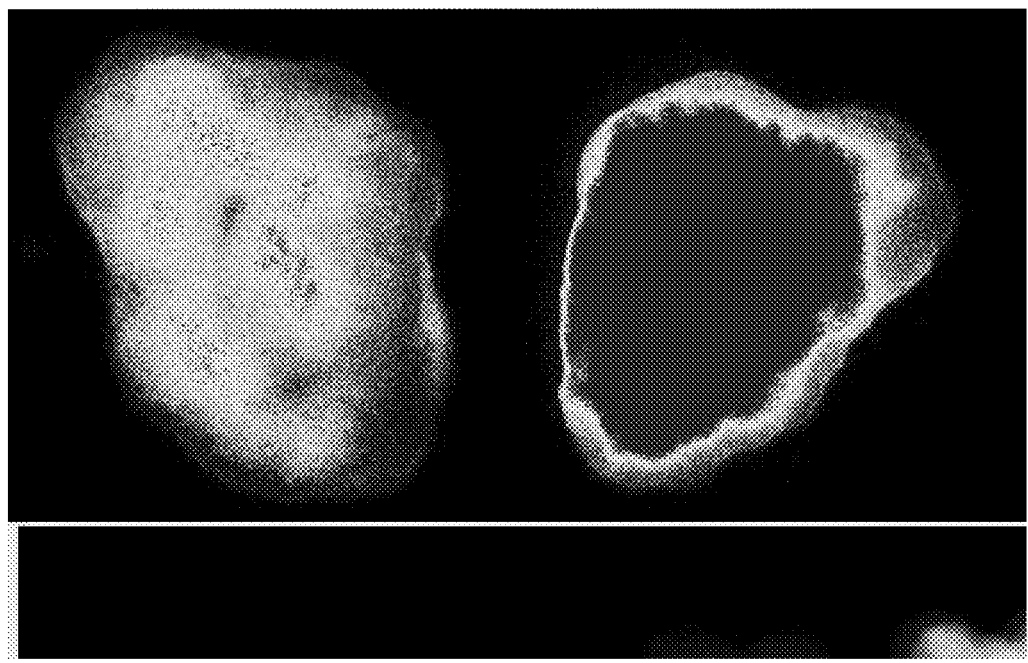
FIG. 17 illustrates the comparison of GB119 (Left) and BMV084 (Right) activation after topical application on explanted Gli36Δ5 xenograft tumors.
Figure 18:
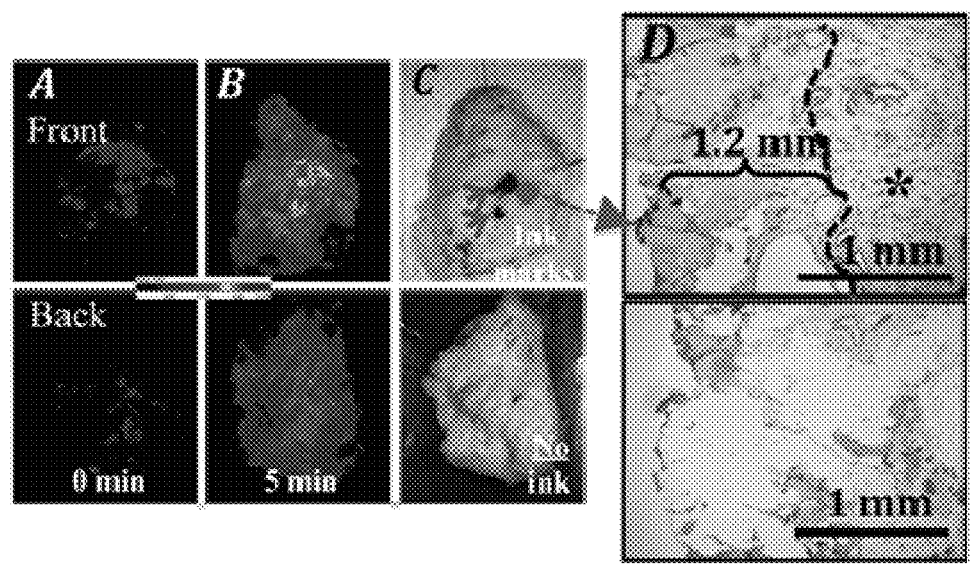
FIGS. 18(A-D) illustrate: (A) Fluorescent images of both the front and back of a lumpectomy specimen prior to BMV084 Application. (B) Fluorescence imaging 5 minutes after probe application. Arrows indicate fluorescent regions where ink was applied. (C) B&W photo showing where ink was applied on the lumpectomy. (D) Top Panel: Histology showing the purple ink (red dotted arrow) and its proximity to cancer, asterisk. Bottom Panel: Histology of normal breast from region that had no fluorescence. Normal ductal tissue is apparent in the lower right of the micrograph. Histology 40× magnification.

We have recently tested a newer quenched NIRF probe (BMV084) that chemically differs from GB119. BMV084 retains cathepsins B and L specificity, can be topically applied, but is approximately 4 times brighter than GB119, FIG. 17. As FIG. 18 shows, BMV084 was topically applied ex vivo to lumpectomy samples resulting in local activation on the lumpectomy sample and these regions were confirmed histologically to be cancerous tissues within the margin, approximately 1 mm from the surface of the lumpectomy, FIG. 18D, and replicates data using GB119 Important to note is that surgical resection of the specimen did not result in global activation of the probe and that little background was observed during this procedure.

TABLE 1

Comparison of topical application of GB119 to detect cancer within the margins of lumpectomy specimens obtained from BCS with imprint cytology or frozen sections.

| | Proposed method (n = 12 specimens) | | Imprint cytology or frozen sections* |
| --- | --- | --- | --- |
| | Per specimen | Per hemisphere | Per specimen |
| Sensitivity | 0.88 | 0.91 | 0.84 |
| Specificity | 1.00 | 0.92 | 0.89 |
| PPV | 1.00 | 0.91 | 0.88 |
| NPV | 0.80 | 0.92 | 0.85 |
| Accuracy | 0.92 | 0.92 | 0.86 |

*Comparators are based on a meta-analysis of 474 patients from studies related to imprint cytology (42-44) and frozen sections (45-47).

Example 3

We tested the ability of a Cathepsin selective quenched NIRF imaging probe, GB119 to be topically applied to freshly isolated prostate biopsies and have demonstrated its ability to be activated by the presence of prostate cancer (PCa). Prostate needle biopsies from patients suspected of harboring prostate cancer removed during standard of care diagnosis were imaged following topical treatment with GB119. The needle biopsy that was confirmed by pathology to be PCa free (FIG. 19A) did not activate the probe. In contrast, a PCa positive biopsy activated GB119 (FIG. 19B). These data indicate the utility of topical application of GB119 to detect PCa.

Having described the invention, I claim:

1. A system for detecting cancer margins, comprising:
a topical protease-specific, fluorescence imaging probe that is activatable by enzymatic activation to produce a visually differentiated signal upon topical application to a targeted cancer cell that secretes an enzyme that activates the protease-specific, fluorescence imaging probe, the probe being selected from the group consisting of GB119 and BMV084;
means for topically administering the imaging probe to the cancer cell; and
an imaging device to detect activation of the imaging probe administered to the cancer cell.

2. The system of claim 1, wherein the protease-specific, fluorescence imaging probe is activated by one of Cathepsin B, and Cathepsin L.

3. The system of claim 1, the system further including an imaging logic to detect a tumor margin, based, at least in part, on the activation of the fluorescent imaging probe.

4. The system of claim 3, the cancer cell being at least one of a breast cancer cell, glioma cell, skin cancer cell, prostate cancer cell, or glioma and the imaging logic detection the breast cancer cell, glioma cell, skin cancer cell, prostate cancer cell, or glioma, based, at least in part, on the activation of the fluorescent imaging probe.

5. The system of claim 1, the system further including a radiologic plan logic to plan a surgical or radiologic treatment based, at least in part, on a detection of a tumor margin, and a detection of an infiltrating cell.

6. The system of claim 1, the system further including an ablative laser plan logic to plan an ablative laser treatment based, at least in part, on a detection of a tumor margin, and a detection of an infiltrating cancer cell.

7. The system of claim 6, the ablative laser plan logic being configured to control, at least in part, an ablative laser.

8. A method, comprising:
topically applying a protease-specific, fluorescence imaging probe to an area in which a cancer cell may be located, the probe being selected from the group consisting of GB119 and BMV084 and being activatable by enzymatic activation to produce a visually differentiated signal upon topical application to the cancer cell, the cancer cell expressing an enzyme that activates the protease-specific, fluorescence imaging probe; and detecting, with an imaging device, imaging probe activation induced by an interaction between the imaging probe and the enzyme expressed by the cancer cell.

9. The method of claim 8, the enzyme being one of, Cathepsin B, and Cathepsin L.

10. The method of claim 8, the cancer cell being at least one of a breast cancer cell, glioma cell, skin cancer cell, prostate cancer cell, or glioma.

11. The method of claim 8, the topical application being conducted in a liquid.

12. The method of claim 8, including:
acquiring an image data associated with the probe activation.

13. The method of claim 8, including determining a radiological or surgical treatment based, at least in part, on the image data.

14. The method of claim 8, including controlling a computer-controllable surgical device based, at least in part, on the image data.

15. The method of claim 8, the surgical device being one of, a laser, a scalpel, a gamma knife, and a micro-electronic machine.

16. A method for performing a medical procedure, comprising:
topically applying a protease-specific, fluorescence imaging probe to an area in which a targeted cancer cell may be located, the imaging probe being selected from the group consisting of GB119 and BMV084 and being activatable by enzymatic activation to produce a visually differentiated signal upon topical application to the cell, the cancer cell expressing an enzyme that activates the protease-specific, fluorescence imaging probe; and
imaging the cell to which the probe is topically applied.

17. The method of claim 16, the enzyme being one of Cathepsin B, and Cathepsin L.

18. The method of claim 16, where topically applying includes spraying the imaging probe onto a tissue sample containing the cell.

19. The method of claim 18, the tissue sample being biopsy that is obtained from an animal.

20. The method of claim 16, the cancer cell being at least one of a breast cancer cell, glioma cell, skin cancer cell, prostate cancer cell, or glioma.

* * * * *